US012411117B2

(12) United States Patent
Huber et al.

(10) Patent No.: US 12,411,117 B2
(45) Date of Patent: Sep. 9, 2025

(54) ANALYSIS DEVICE FOR GASES IN A COMPRESSED-GAS TANK

(71) Applicant: BAUER KOMPRESSOREN GmbH, Munich (DE)

(72) Inventors: Johannes Huber, Friedberg (DE); Thomas Burmeister, Sachsenkam (DE); Robert Kampfl, Munich (DE); Stefanie Frantz, Munich (DE)

(73) Assignee: BAUER KOMPRESSOREN GMBH, Munich (DE)

(*) Notice: Subject to any disclaimer, the term of this patent is extended or adjusted under 35 U.S.C. 154(b) by 504 days.

(21) Appl. No.: 17/800,821

(22) PCT Filed: Feb. 18, 2021

(86) PCT No.: PCT/EP2021/054032
§ 371 (c)(1),
(2) Date: Aug. 18, 2022

(87) PCT Pub. No.: WO2021/165399
PCT Pub. Date: Aug. 26, 2021

(65) Prior Publication Data
US 2023/0077827 A1 Mar. 16, 2023

(30) Foreign Application Priority Data
Feb. 19, 2020 (DE) .................. 10 2020 001 077.6

(51) Int. Cl.
G01N 33/00 (2006.01)
F17C 13/02 (2006.01)
G05D 16/20 (2006.01)

(52) U.S. Cl.
CPC ......... G01N 33/0063 (2013.01); F17C 13/02 (2013.01); G01N 33/0009 (2013.01);
(Continued)

(58) Field of Classification Search
CPC ........... G01N 33/0063; G01N 33/0009; G01N 33/0016; G05D 16/2066; Y02A 50/20; F17C 13/02; F17C 2221/03
See application file for complete search history.

(56) References Cited

U.S. PATENT DOCUMENTS 5,027,642 A    7/1991  Wen et al.
5,810,928 A *  9/1998  Harada .................. C23C 16/52
                                                    118/712
(Continued)

FOREIGN PATENT DOCUMENTS

CN    202 188 978 U    4/2014
CN    207 294 167 U    5/2018
(Continued)

OTHER PUBLICATIONS

International Search Report issued in PCT/EP2021/054032 dated May 18, 2021, 4 pages.

Primary Examiner — William M McCalister
(74) Attorney, Agent, or Firm — Rothwell, Figg, Ernst & Manbeck, P.C.

(57) ABSTRACT

The present invention relates to an analysis apparatus for compressed gases in a compressed-gas tank, such as a breathing-air cylinder or the like, for determining gas components, in particular CO, $CO_2$, $O_2$, VOC, $SO_2$, NO, $NO_2$, helium and moisture, having a removal device which can be connected to the compressed-gas tank, characterised in that the removal device comprises a connection element which is under the pressure of the compressed gas to be analysed in the compressed-gas tank and can be coupled to a gas treatment device having a gas measuring and evaluating device for determining the desired gas components, the connection element is also pressurised when not connected to the compressed-gas tank, preferably by means of a shut-off valve, and the gas treatment device and the gas
(Continued)

measuring and evaluating device are further also configured to monitor and analyse the compressed gases dispensed by a compressor to fill a compressed-gas tank.

20 Claims, 3 Drawing Sheets

(52) U.S. Cl.
CPC ..... *G01N 33/0016* (2013.01); *G05D 16/2066* (2013.01); *F17C 2221/03* (2013.01); *Y02A 50/20* (2018.01)

(56) References Cited

U.S. PATENT DOCUMENTS

| | | | |
|---|---|---|---|
| 5,908,053 A | 6/1999 | Byrd | |
| 7,108,009 B2* | 9/2006 | Ishida | G05D 7/0658 |
| | | | 702/100 |
| 2015/0075255 A1* | 3/2015 | Yabe | G01N 33/0036 |
| | | | 73/29.05 |
| 2016/0116115 A1* | 4/2016 | Leavitt | F17C 13/003 |
| | | | 206/459.5 |
| 2018/0134203 A1* | 5/2018 | Durak | B60P 3/227 |
| 2019/0049388 A1* | 2/2019 | Jensen | G01N 21/01 |
| 2019/0120431 A1 | 4/2019 | Carroll et al. | |
| 2019/0220720 A1* | 7/2019 | Durak | G06K 19/04 |
| 2020/0141887 A1 | 5/2020 | Kampfl | |
| 2021/0372978 A1* | 12/2021 | Iwaya | G01N 33/0062 |
| 2023/0077827 A1* | 3/2023 | Huber | G01N 33/0063 |
| | | | 137/14 |

FOREIGN PATENT DOCUMENTS

| | | |
|---|---|---|
| DE | 38 89 840 T2 | 9/1994 |
| DE | 698 37 504 T2 | 12/2007 |
| DE | 20 2017 000 121 U1 | 3/2017 |
| DE | 10 2018 008 636 A1 | 5/2020 |
| EP | 3346128 A1 | 7/2018 |

* cited by examiner

ANALYSIS DEVICE FOR GASES IN A COMPRESSED-GAS TANK

This application is a 35 U.S.C. 371 National Phase Entry Application from PCT/EP2021/054032 filed Feb. 18, 2021, which claims priority to and the benefit of German Patent Application No. 10 2020 001 077.6, filed on Feb. 19, 2020, the disclosures of which are incorporated herein by reference in their entirety.

The invention relates to an analysis apparatus for compressed gas in a compressed-gas tank, such as a breathing-air cylinder or the like. Said analysis apparatus serves for determining gas components, in particular CO, $CO_2$, $O_2$, VOC, $SO_2$, NO, $NO_2$, helium and moisture, and has a removal device that can be connected to the compressed-gas tank.

The concentration as well as the composition and the pressure of the compressed gas in the compressed-gas tank are unknown, unless a separate gas measuring device is used for the compressed-gas tank. The gas measuring devices and in particular those that also record the moisture, for example by means of a dew point sensor, are relatively expensive to purchase and maintain.

Furthermore, it is known from the prior art, for example from DE 10 2018 008 636 A1, to constantly measure the air quality of a compressor for filling such a compressed-gas tank, whereby this can be both a portable compressed-gas tank, such as a breathing-air cylinder or the like, or also a permanently installed compressed-gas tank. The monitoring of a compressor has the advantage that the constant flow of gas through the corresponding measuring apparatus means that the conditions therein remain the same and less moisture accumulates in the system due to the pressurised pipelines.

The invention therefore aims to provide a more cost-effective and reliable analysis apparatus of the generic type, while overcoming the difficulties described above, which analysis apparatus can promptly, quickly and reliably record the gas components, the pressure and the moisture both from a compressor and from a pressure vessel/tank by means of a separate gas measuring and evaluating device.

A challenge here can be to load not only the corresponding sensor but also all feed lines to the pre-dried sensor system with as little moisture as possible in order to achieve the shortest possible rinsing time.

According to the invention, an analysis apparatus for compressed gases in a compressed-gas tank, such as a breathing-air cylinder or the like, for determining gas components, in particular CO, $CO_2$, $O_2$, VOC, $SO_2$, NO, $NO_2$, helium and moisture, is provided, having a removal apparatus that can be connected to the compressed-gas tank. This analysis apparatus is characterised in that the removal device comprises a connection element which is under the pressure of the compressed gas to be analysed in the compressed-gas tank and can be coupled to a gas treatment device having a gas measuring and evaluating device for determining the desired gas components, wherein, if appropriate, the connecting element comprises a desiccant, if possible in the atmospheric range, in that the connection element is also pressurised when not connected to the compressed-gas tank, preferably by means of the shut-off valve, and the gas treatment device and the gas measuring and evaluating device are further also configured to monitor and analyse the compressed gases dispensed by a compressor to fill a compressed-gas tank.

The desiccant can be used to keep the pre-drying of the components exposed to the atmosphere dry during standstill. Thus, the waiting time is reduced substantially until a meaningful measurement is possible.

In the analysis apparatus according to the invention, the gas device is used with an evaluating device for determining the desired gas components, via a connection element in the removal device, which evaluating device is already present, and the gases dispensed from the compressor analysed. Thus, in the invention, the gas measuring device is used together with an evaluating device which is present in the compressor system. This allows the acquisition and maintenance costs to be reduced.

Further advantageous configurations of the analysis apparatus according to the invention are given in the dependent claims.

In particular, it is essential in the analysis apparatus according to the invention that the connection element and all regions which come into contact with the compressed gas have moisture-repellent properties, so that the desired values can be recorded as promptly as possible and as far as possible without any negative influence of the moisture present in the atmosphere. It is also expedient to use suitable materials which have moisture-repellent properties for the connection element and the associated parts. This is, for example, stainless steel or the like. In the case of a connection element in the form of a connection hose, this preferably has a PTFE or FEP core.

Such a gas measuring device preferably includes a moisture sensor, for example a dew point sensor which is relatively expensive and sensitive, and, at the same time in the invention, this sensor of the gas measuring device records the gas analysis of the compressed gas in the compressed-gas tank.

In order to prevent falsifications or operating errors, the pressure tank comprises an RFID chip identifying the serial number or another uniquely identifying, readable code CQR, barcode or the like. This code can be read using a reader on the removal device, and the code is preferably transferred to a cloud storage device or another data storage medium, such as a USB stick or the like.

The evaluating device of the gas measuring device is preferably designed in such a way that the signal relating to the gas components is also transmitted to the cloud storage device or another data storage medium, in particular by means of remote transmission. Thus, the most important pieces of information regarding the gas composition can be stored with corresponding assignment to a specific compressed-gas tank, which information can also be read out again from the cloud storage device or another storage medium in order to document the measured and analysis values.

In one embodiment of the analysis apparatus according to the invention, a first and a second controllable valve can be provided for connection to the compressor and the compressed-gas tank, wherein at least one of the controllable valves can preferably be formed by a solenoid valve.

While it would be possible in principle to provide the controllable valves in the high-pressure region, since, for example, high-pressure solenoid valves are available that work in pressure ranges of up to 550 bar, a pressure reducer can also be connected upstream of the two valves. In such an embodiment, each of the two high-pressure regions of the compressor or compressed-gas tank can then be connected to the gas treatment device and thus to the gas measuring and evaluating device via its own gas removal unit, comprising a pressure reducer, a nozzle, a safety valve and a controllable valve, in particular a solenoid valve.

Furthermore, the analysis apparatus according to the invention can also comprise control logic which is configured to ensure that only one of the controllable valves can be open at a time, since otherwise the two analysis gas flows can mix, which could result in incorrect measurements.

The analysis apparatus according to the invention can preferably be integrated in the compressor which then accordingly comprises such an analysis apparatus as a permanently installed component. In particular, the analysis apparatus can be integrated in the compressor in such a way that, during operation thereof, it carries out constant monitoring of the discharged compressed gases.

According to a further aspect, the present invention relates to a method for operating an analysis apparatus according to the invention, wherein, in a first operating mode of the analysis apparatus, the gas measuring and evaluating device monitors and analyses the compressed gases dispensed by a compressor for filling a compressed-gas tank, while, in a second operating mode of the analysis apparatus, the gas measuring and evaluating device monitors and analyses compressed gases dispensed by the compressed-gas tank.

In this case, switching between the first operating mode and the second operating mode can take place by manual switching, and/or at least one of the following events can be triggered during the switching in order to avoid security gaps in the monitoring of the compressor, in particular when a measurement of the compressor is switched to a measurement of the compressed-gas tank:
  the compressor is switched off or prevented from starting via an alarm contact; for this purpose, there must be an operational link between the controller of the compressor and of the gas treatment device;
  a rinsing valve is opened so that the compressed gas provided by the compressor escapes and is not filled into the compressed-gas tank; for this purpose, a corresponding rinsing valve must be provided for the compressor;
  the current operating mode is signalled so that no unintentional operation of the compressor is possible; for this purpose, a correspondingly configured and coupled display or signalling apparatus is required.

Further details, features and advantages of the invention result from the following description of preferred embodiments with reference to the attached drawings in which.

Figure 1:
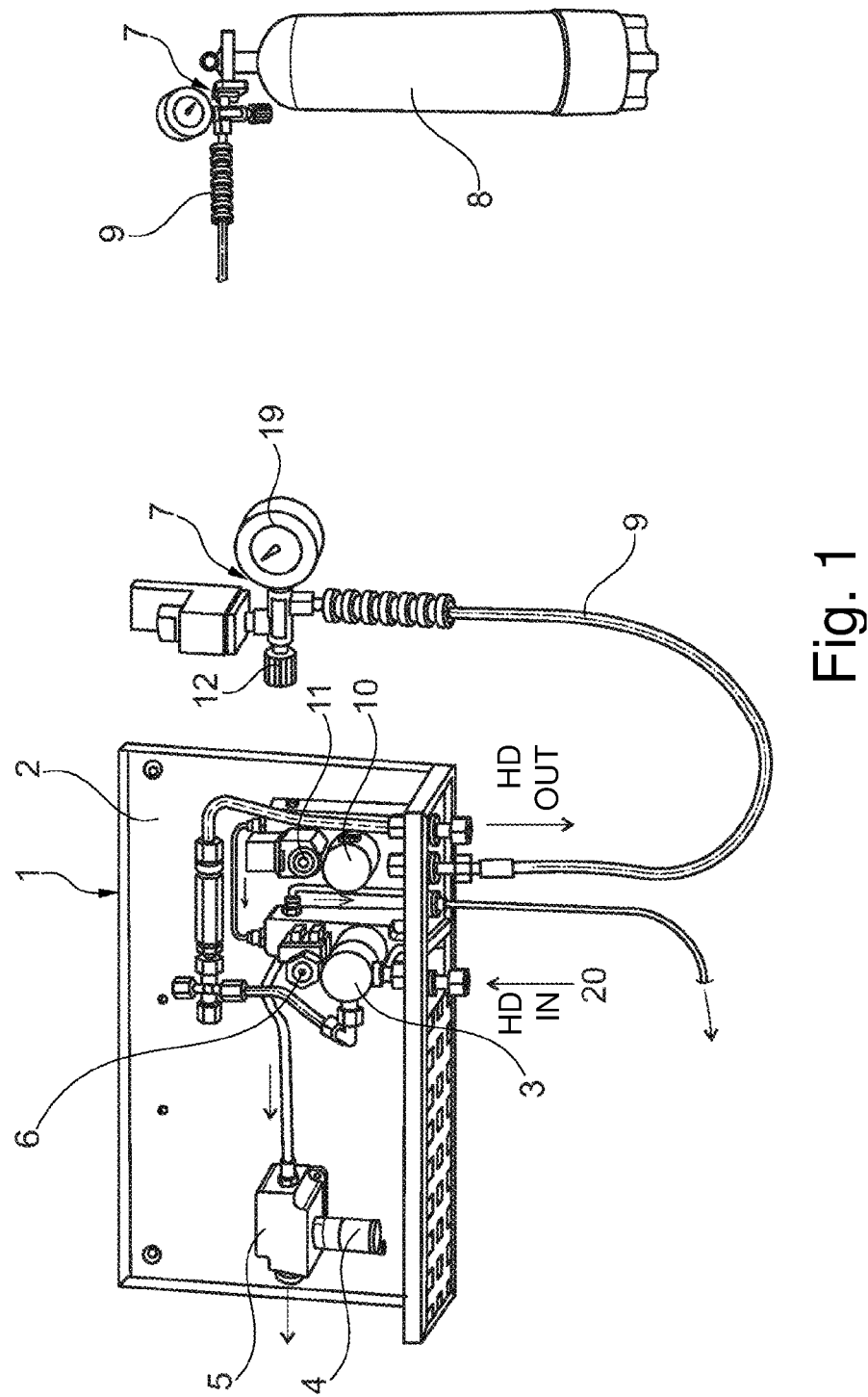
FIG. 1 is a schematic view of a preferred embodiment according to the invention, on the one hand having a compressed-gas tank connection element and on the other hand in the basic state and uncoupled from the compressed gas tank.

The left-hand part of FIG. 1 shows an analysis apparatus, denoted as a whole by 1. This analysis apparatus 1 comprises a gas treatment device which is denoted as a whole by 2. As indicated by HD-IN and HD-OUT, this is the input of the high-pressure gas supplied by the compressor, for example, which exits via HD-OUT after passing through the gas treatment device 2. A pressure reducer for the compressed gases coming from the high-pressure compressor is denoted by 3. Furthermore, the gas treatment device 2 comprises a dew point sensor 4, a moisture measuring unit 5 which contains a desiccant (not shown in detail) and a flow sensor. A solenoid valve 6 is connected downstream of the pressure reducer 3.

Also shown in this drawing is a removal device 7 which can be connected to a compressed-gas tank 8 in the form of a breathing-air cylinder, for example via a connection element 9. The left-hand part of FIG. 1 shows the removal device 7 having the connection element 9 in the form of a connection hose uncoupled from the compressed-gas tank 8. The connection element 9 establishes a coupling connection to the gas treatment device 2, and a communicating line connection to the dew point sensor 4 of the moisture measuring unit 5 is established via a pressure reducer and a solenoid valve 6.

In the solution according to the invention, the gas treatment device is used in the analysis apparatus 1, which gas treatment device is provided for the compressor (not shown in detail here).

The removal device is explained in more detail below with reference to the drawings in FIG. 2.

It is important that the connection element 9 is also pressurised when not connected to the compressed-gas tank, preferably by means of a shut-off valve.

Figure 2:
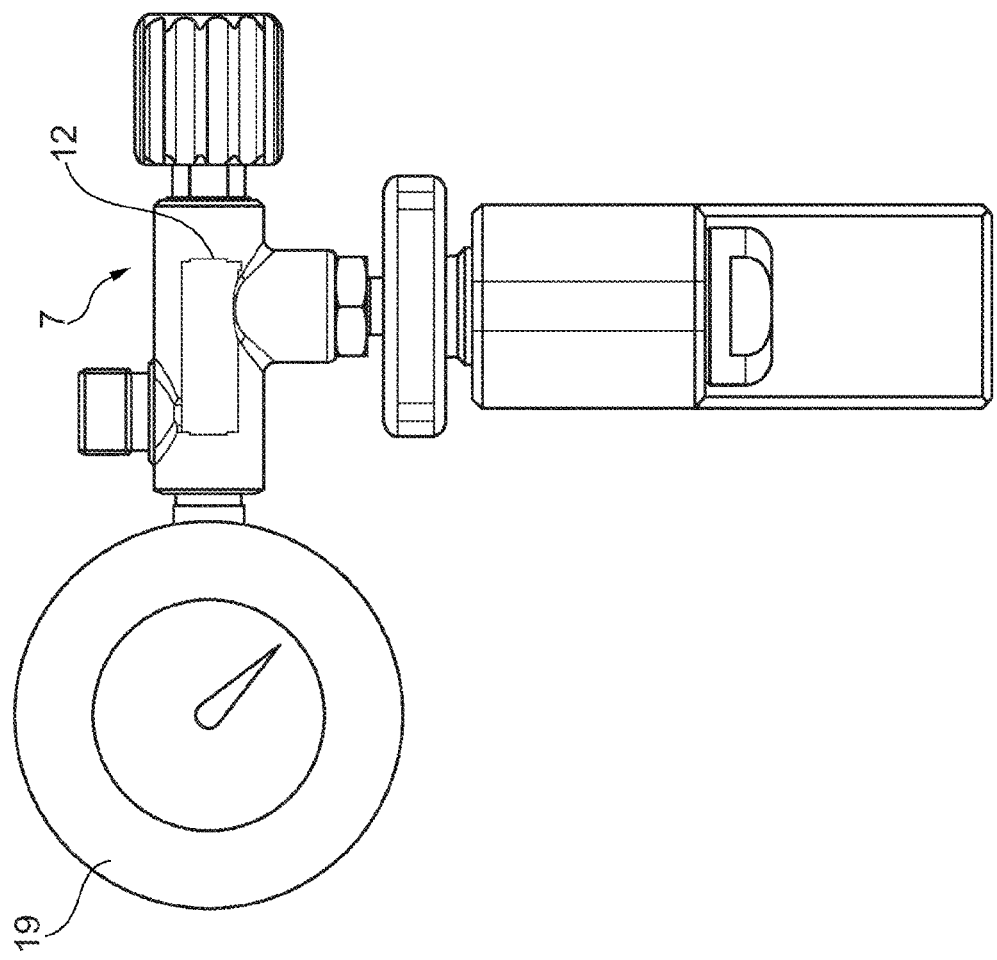
FIG. 2 is a side view and sectional view of the connection element to be coupled to the compressed-gas tank.
Figure 2:
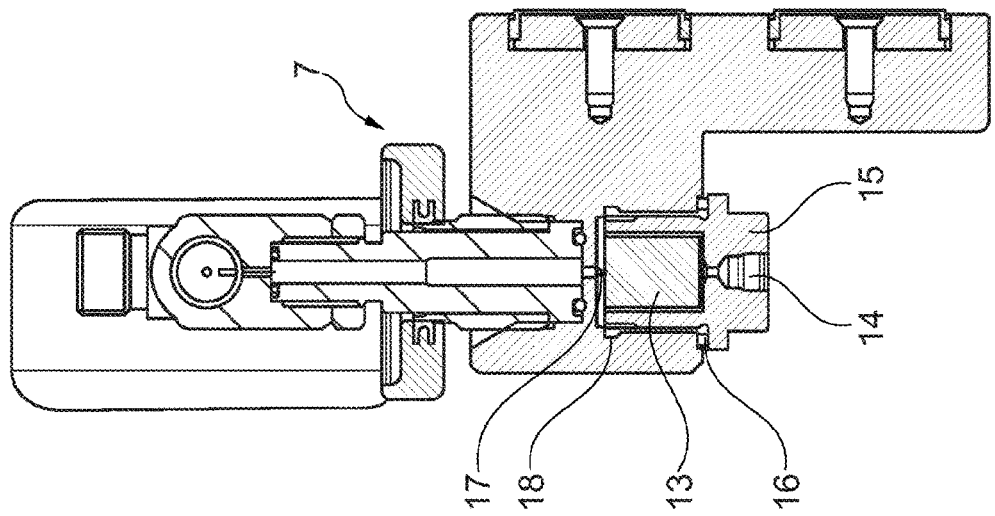

From the two views of FIG. 2, it can be seen that the removal device 7 has a desiccant (drying capsule) 13, a non-return valve 14, a locking screw 15, a metal seal 16, a nozzle 17 and an elastomer seal. The shut-off valve 12 is also shown here as a double-sided shut-off valve. A manometer 19 is also assigned to the removal device 7. The removal device 7 is designed according to the sectional view in FIG. 2 in such a way that the connection element 9 is moisture-repellent with regard to the inner passage, so that the gas treatment device 2 (FIG. 2) can be used to record timely and reliable measurement results which are largely free of influences from atmospheric moisture.

Figure 3:
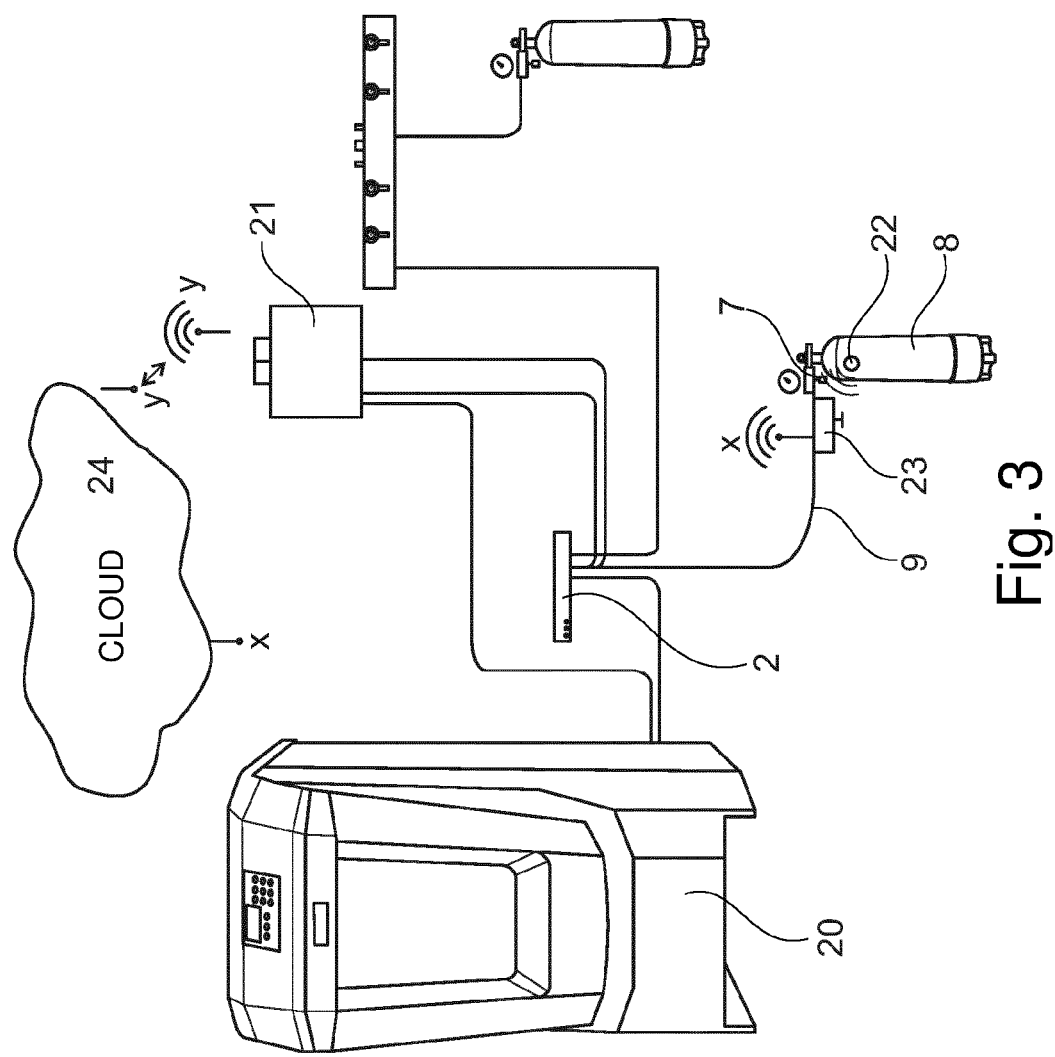
FIG. 3 is a schematic overall view of a compressor system having a measuring device and an evaluating device which is also used in the invention for analysing and determining the components of the compressed gas in the compressed-gas tank.

FIG. 3 is a schematic overall view of the concept according to the invention. A gas treatment device 2 is connected to a compressor 20, which gas treatment device is shown in FIG. 1, for example, with regard to its more detailed structure. This gas treatment device 2 is connected to a gas measuring and evaluating device 21 which evaluates the measured data recorded with the aid of the gas measurement sensor system in more detail.

As can be seen from the schematic representation of FIG. 3, the compressed-gas tank 8 in the form of a breathing-air cylinder has an RFID chip which includes, for example, the unique serial number of the compressed-gas tank 8. The information on the RFID chip 22 is read out with the aid of a reader 23 and, as indicated schematically by X, is transmitted to a cloud storage device 24 via remote transmission. Alternatively, another readable code, CQR, barcode or the like, which clearly identifies the compressed-gas tank 8, could be selected. The gas measuring and evaluating device 21 also transmits the evaluated data to the cloud storage device 24 by remote transmission which is indicated schematically by Y. Alternatively, the data can also be transferred to another external storage medium.

Thus, in the cloud storage device 24, for example, the corresponding results of the gas measuring and evaluating device 21 are clearly assigned to the compressed-gas tank 8, namely via the RFID chip, so that the recorded data are brought together in the cloud storage device 24 or another external storage medium.

Of course, the invention is not limited to the details shown and explained above, but numerous alterations and modifications are possible, which a person skilled in the art will make, if necessary, without departing from the concept of the invention.

LIST OF REFERENCE SIGNS

1 Analysis apparatus as a whole
2 Gas treatment device
3 Pressure reducer
4 Moisture sensor, for example dew point sensor
5 Moisture measuring unit
6 Solenoid valve
7 Removal device
8 Compressed-gas tank in the form of a breathing-air cylinder
9 Connection element, preferably in the form of a connection hose
10 Pressure reducer
11 Solenoid valve
12 Shut-off valve
13 Desiccant
14 Non-return valve
15 Locking screw
16 Metallic seal
17 Nozzle
18 Elastomer seal
19 Manometer
20 Compressor
21 Gas measuring and evaluating device
22 RFID chip
23 Reader
24 Cloud storage device

The invention claimed is:

1. A method for operating an analysis apparatus comprising a removal device capable of being connected to a compressed-gas tank, a connection element that is under the pressure of compressed gases in the compressed-gas tank when connected to the compressed-gas tank and pressurized when not connected to the compressed-gas tank, and a gas treatment device to which the connection element is capable of being connected, wherein the gas treatment device comprises a gas measuring and evaluating device for determining gas components, the method comprising:
  operating the analysis apparatus in a first operating mode in which the gas measuring and evaluating device monitors and analyses compressed gases dispensed by a compressor, and
  operating the analysis apparatus in a second operating mode in which the gas measuring and evaluating device monitors and analyses compressed gases dispensed by the compressed-gas tank.

2. The method according to of claim 1, characterised in that further comprising switching between the first operating mode and the second operating mode.

3. The method of claim 2, wherein the switching between the first operating mode and the second operating mode takes place by manual switching.

4. The method of claim 2, wherein the switching comprises at least one of:
  switching off the compressor or preventing the compressor from starting via an alarm contact;
  opening a rinsing valve to allow compressed gas provided by the compressor to escape instead of filling the compressed-gas tank; and
  signalling a current operating mode of the analysis apparatus to prevent unintentional operation of the compressor.

5. The method of claim 1, wherein the connection element comprises a desiccant in the atmospheric region for pre-drying the components exposed to the atmosphere during standstill.

6. The method of claim 1, wherein the connection element and all regions that come into contact with the compressed gas have moisture-repellent properties.

7. The method of claim 1, wherein the connection element comprises a connection hose.

8. The method of claim 7, wherein the connection hose has a PTFE or FEP core configured to repel moisture.

9. The method of claim 1, wherein the gas treatment device comprises a moisture sensor.

10. The method of claim 1, further comprising:
  using a reader on the removal device to read an RFID chip that identifies a serial number; and
  transmitting the serial number to a cloud storage device.

11. The method of claim 1, further comprising using the gas measuring and evaluating device to transmit signals relating to the gas components to a cloud storage device by means of remote transmission.

12. The method of claim 5, wherein a nozzle is connected upstream of the desiccant, and the nozzle is configured to prevent rapid entry of ambient moisture into a measuring region.

13. The method of claim 5, further comprising removing the desiccant by means of a locking screw.

14. The method of claim 1, wherein the analysis apparatus further comprises a first controllable valve and a second controllable valve for connection to the compressor and the compressed-gas tank, respectively.

15. The method of claim 14, wherein at least one of the first and second controllable valves is formed by a solenoid valve.

16. The method of claim 14, wherein a first pressure reducer is connected upstream of the first controllable valve and a second pressure reducer is connected upstream of the second controllable valve.

17. The method of claim 14, further comprising using control logic of the analysis apparatus to ensure that only one of the first and second controllable valves is capable of being open at any time.

18. The method of claim 1, wherein the compressed-gas tank is a breathing-air cylinder.

19. The method of claim 1, wherein the determined gas components comprise CO, CO2, O2, VOC, SO2, NO, NO2, helium, and/or moisture.

20. The method of claim 1, wherein a shut-off valve pressurizes the connection element when not connected to the compressed-gas tank.

* * * * *